United States Patent
Lin et al.

(10) Patent No.: US 12,389,914 B2
(45) Date of Patent: *Aug. 19, 2025

(54) ENDOPHYTIC FALCIPHORA ORYZAE FO-R20 AND ITS APPLICATION

(71) Applicant: ZHEJIANG ACADEMY OF AGRICULTURAL SCIENCES, Zhejiang (CN)

(72) Inventors: Fucheng Lin, Hangzhou (CN); Zhenzhu Su, Hangzhou (CN); Lin Li, Hangzhou (CN); Yan Liang, Hangzhou (CN); Kunlun Shen, Hangzhou (CN)

(73) Assignee: ZHEJIANG ACADEMY OF AGRICULTURAL SCIENCES, Hangzhou (CN)

( * ) Notice: Subject to any disclaimer, the term of this patent is extended or adjusted under 35 U.S.C. 154(b) by 146 days.

This patent is subject to a terminal disclaimer.

(21) Appl. No.: 17/744,713

(22) Filed: May 15, 2022

(65) Prior Publication Data
US 2022/0369648 A1   Nov. 24, 2022

(30) Foreign Application Priority Data
May 14, 2021 (CN) .......................... 202110529929.3

(51) Int. Cl.
   *A01N 63/30*   (2020.01)
   *A01C 1/06*    (2006.01)
   *A01G 22/22*   (2018.01)
   *A01G 24/20*   (2018.01)
   *C12N 1/14*    (2006.01)

(52) U.S. Cl.
   CPC ............... *A01N 63/30* (2020.01); *A01C 1/06* (2013.01); *A01G 22/22* (2018.02); *A01G 24/20* (2018.02); *C12N 1/145* (2021.05)

(58) Field of Classification Search
   CPC ........ A01N 63/30; A01G 24/20; A01G 22/22; C12N 1/145; A01C 1/06
   See application file for complete search history.

(56) References Cited

U.S. PATENT DOCUMENTS

| | | | | |
|---|---|---|---|---|
| 2010/0144534 A1* | 6/2010 | Pullen | ................... | A01N 31/00 47/58.1 SC |
| 2012/0021906 A1* | 1/2012 | Sutton | ................... | C05F 11/08 424/490 |
| 2017/0245503 A1* | 8/2017 | Ashby | ................... | C12N 1/20 |

FOREIGN PATENT DOCUMENTS

| CN | 101779574 | * | 7/2010 |
|---|---|---|---|
| CN | 107593319 | * | 1/2018 |

OTHER PUBLICATIONS

Yuan et al. FEMS Microbiol Lett vol. 307, pp. 94-101 (Year: 2010).*
NCBI accession No. NR_153972 [online]. NCBI [retrieved on Apr. 10, 2024] retrieved from the internet: <https://www.ncbi.nlm.nih.gov/nuccore/NR_153972.1/>. (Year: 2024).*
Falciphora oryzae entry Taxonomy ID: 1609947 NCBI Taxonomy Browser Website [online]. NCBI [Retrieved on Apr. 10, 2024]. Retrieved from the internet: <https://www.ncbi.nlm.nih.gov/Taxonomy/Browser/wwwtax.cgi?id=1609947>. (Year: 2024).*
English Machine Translation of Li CN101779574 [online]. Google Patents [Retrieved on Apr. 10, 2024]. Retrieved from the internet: <https://patents.google.com/patent/CN101779574B/en?oq=CN101779574>. (Year: 2024).*
English Machine Translation of Li CN 107593319 [online]. Google Patents [retrieved on Apr. 11, 2024]. Retrieved from the internet: <https://patents.google.com/patent/CN107593319A/en?oq=CN+107593319>. (Year: 2024).*
Su et al. Mycosystema vol. 38 No. 11. (Year: 2019).*
Human Assisted Machine Translation of Su et al. Mycosystema vol. 38 No. 11 Provided to the USPTO on Apr. 10, 2024. (Year: 2024).*

* cited by examiner

*Primary Examiner* — Katherine Peebles
(74) *Attorney, Agent, or Firm* — Jiwen Chen; Joywin IP Law PLLC

(57) ABSTRACT

The present invention discloses an endophytic fungus FO-R20 and applications thereof, and belongs to the technical filed of microbial applications. The deposit number of the endophytic fungus FO-R20 is CCTCC M 2021505, and the scientific name thereof is *Falciphora oryzae*. The present invention provides a novel endophytic fungal strain in the genus *Phialophora*. Colonization of the endophytic fungus FO-R20 in the root tissues of rice can significantly improve the quality of rice seedlings and enhance the rice yields. The remarkable effect of symbiosis and interactions of the endophytic fungus FO-R20 on rice has huge value in the agricultural field by application and popularization thereof.

4 Claims, 9 Drawing Sheets
Specification includes a Sequence Listing.

SEQUENCE LISTING

<160> NUMBER OF SEQ ID NOS: 3

<210> SEQ ID NO 1
<211> LENGTH: 527
<212> TYPE: DNA
<213> ORGANISM: Falciphora oryzae

<400> SEQUENCE: 1

```
cggagggatc attaaagagt tgaaaaactc caacccctgt gaaccttacc tttactgttg      60
cttcggcgga cgacggccct tcgtggcccg aggccgccgg aggttccaaa ctctaaatct     120
ttagtgtatc tctgaggaaa ataaaccaat aattaaaact ttcaacaacg gatctcttgg     180
ttctggcatc gatgaagaac gcagcgaaat gcgataagta atgtgaattg cagaattcag     240
tgaatcatcg aatctttgaa cgcacattgc gcccgccggt attccggcgg gcatgcctgt     300
tcgagcgtca tttcaccact caagcccagc ttggtgttgg ggcacccggc cgccggcgg     360 tcggggcccc caagtacatc ggcggtctcg ctaggaccct gagcgcagta actcgcggta     420
aaacgcgcct cgctcggaag ttcccagcgg gcttccagcc gctaaacccc ccctaatttt     480
cttaggttga cctcggatca ggtaggaata cccgctgaac ttaagca                   527
```

<210> SEQ ID NO 2
<211> LENGTH: 19
<212> TYPE: DNA
<213> ORGANISM: Artificial Sequence
<220> FEATURE:
<223> OTHER INFORMATION: Synthesized

<400> SEQUENCE: 2

```
tccgtaggtg aacctgcgg                                             19

<210> SEQ ID NO 3
<211> LENGTH: 20
<212> TYPE: DNA
<213> ORGANISM: Artificial Sequence
<220> FEATURE:
<223> OTHER INFORMATION: Synthesized

<400> SEQUENCE: 3
tcctccgctt attgatatgc                                            20
```

ENDOPHYTIC FALCIPHORA ORYZAE FO-R20 AND ITS APPLICATION

This application claims priority to Chinese Patent Application No. 2021105299293 filed May 14, 2021, which is hereby incorporated by reference.

FIELD OF TECHNOLOGY

The present invention relates to the technical field of microbiological applications and, in particular, to an endophytic fungus FO-R20 and its application thereof in improving the quality of rice seedlings and/or enhancing rice yields.

BACKGROUND TECHNOLOGY

There are a lot of beneficial microorganisms hiding in the ecological system of the nature, among which are the endophytic fungi in plants. The endophytic fungi in plants refer to a group of fungi which can invade and colonize healthy plant tissues during at least a part of the life cycle thereof without causing apparent disease symptoms in the host. Commonly existing in ecological systems, the endophytic fungi have very stable long-term interactions with the host plants. During the formation of the mutualism between the endophytic fungi in plants and the hosts, on one hand, the endophytic fungi in plants obtain water and mineral nutrients among other nutrients required for growth from the hosts, while on the other hand, the endophytic fungi in plants also provide the plants with various biological functions, such as promoting the growth of the plants, improving the biomass of the plants, and enhancing the resistance of the host plants against biotic and abiotic stresses. With the gradually growing attention on studies of the endophytic fungi, the study of symbiosis and interaction mechanism between plants and endophytic fungi has become a new international research hotspot.

Rice is the most important food crop in China, and hence achieving stable and high yields of rice is the basis of the sustainable development in China. In recent years, with the in-depth understanding of micro ecosystems in plants, it has been found that the phenotypes of plants are not only influenced by their own genetic characteristics, but also actively regulated by the surrounding beneficial microorganisms. The symbiosis and interactions between plants and endophytic fungi are one of the typical examples, wherein the endophytic fungi can not only promote a plant's vegetative growth and increase of biomass, but also improve a host's resistance to biotic and abiotic stresses, thereby having good prospects for agroecological applications. Reconstruction of a beneficial symbiosis system between rice and endophytic fungi by using endophytic fungi from wild rice is one of the ways to effectively promote rice growth and improve rice yields and stress resistance. Therefore, constructing a mutualistic symbionts between rice and endophytic fungi from wild rice is of great significance for improving the rice yields and promoting a sustainable development of agriculture.

Currently, mechanical transplanting of rice is promoted and popularized rapidly in China, which poses an even more stringent requirement for the quality of rice seedlings. Therefore, it has become the biggest technical obstacle to cultivate robust seedlings which are not only suitable for operations of mechanical transplanting of rice, but meet the requirements of high-yielding agronomy. As demonstrated by a Chinese saying, "good seedlings promise half of the yields", one important technical measure to promote high yields of rice is to improve the quality of rice seedlings and produce healthy and strong seedlings. At present, the seedlings raised in production are not strong enough, hard to meet the operational standards of transplanters, resulting in poor quality of planting, slow growth resuming after transplanting, which in turn leads to low yields. Therefore, explorations of microorganisms that can improve the quality of rice seedlings and strengthen seedlings, and application methods thereof, will further help the development of mechanical transplanting of rice.

However, there is no report yet so far of functions of endophytic fungi derived from wild rice in improving the quality of rice seedlings and enhancing the rice yields, or of application methods thereof in the fields.

SUMMARY OF THE INVENTION

The object of the present invention is to provide a novel endophytic fungal strain and to achieve stable and high yields of rice by using the symbiosis and interactions between the strain and rice.

To achieve the above object, the following technical scheme is adopted herein.

An endophytic fungal strain belonging to the genus *Phialophora* was isolated from the root system of wild rice *Oryza granulate* collected from Yunnan Province. The ITS sequence of the endophytic fungal strain is as set forth in SEQ ID No.1, and the morphological characteristics thereof are that, the colony grows slowly on a PDA plate and the colony diameter reaches 6 cm after growing at 25° C. for 10 days; aerial mycelia are poorly developed, prostrating on the medium surface, the colony is brown, the mycelia are hyaline or dark brown, 1.0-2.5 µm in width; conidiophores are bottle-shaped, solitary, unbranched, 5.0-13.5×2.5-3.0 µm; conidia are sickle-shaped, colorless, no septum, 7.0-9.0×0.8-1.2 µm. The strain was identified as belonging to the genus *Phialophora* in the family Magnaporthaceae in the class Sordariomycetes in the phylum Ascomycota in the kingdom Fungi, and was designated with the scientific name *Falciphora oryzae* FO-R20. The strain was deposited on May 8, 2021 in the China Center for Type Culture Collection (CCTCC) at Wuhan University in Wuhan, China, the recognized IDA under the Budapest Treaty on the International Recognition of the Deposit of Microorganisms for the Purposes of Patent Procedure, under the deposit number of CCTCC M 2021505, and the scientific name thereof is *Falciphora oryzae*.

The culture conditions for the endophytic fungus FO-R20 are: inoculation of the mycelia of the endophytic fungus FO-R20 on a PDA solid culture medium and incubation at 25° C. in the dark for 5 days.

Further provided in the present invention are two forms of preparations of the endophytic fungus FO-R20, one of which is a seed coating agent prepared with the endophytic fungus to coat crop seeds such that the endophytic fungus FO-R20 colonizes the roots of plant seedlings during the process of seedling raising; and the other form is a solid fungal fertilizer prepared with the endophytic fungus, wherein the solid fungal fertilizer is mixed with a seedling substrate, and germinated crop seeds are sown in the seedling substrate containing the endophytic fungus FO-R20 such that the endophytic fungus FO-R20 colonizes the roots of plant seedlings during the process of seedling raising.

The present invention further provides a preparation method of the seed coating agent with endophytic fungus FO-R20, the method comprising: obtaining a seed coating agent after mixing well mycelia of an endophytic fungus FO-R20 under the deposit number CCTCC M 2021505 and a chitosan solution.

Preferably, the endophytic fungal strain FO-R20 is inoculated in a PDA medium and cultured at 25° C. in the dark, and then inoculated in a liquid fermentation medium and cultured at 25° C. to obtain mycelia of the endophytic fungus FO-R20; then the mycelia are mixed with a chitosan solution at a mass percentage concentration of 1% in a ratio of 1 g:10 L to obtain the seed coating agent; the mass of the mycelia is measured by dry weight. The 1% chitosan solution is prepared by dissolving 1 g of chitosan in 100 mL 1% acetic acid solution.

The liquid fermentation medium contains 0.4% of soybean cake flour, 1% of corn flour, 0.05% of magnesium sulfate and 0.1% of dipotassium phosphate per 250 mL of the medium by mass percentage.

The present invention provides a preparation method of the solid fungal fertilizer with the endophytic fungus FO-R20, the method comprising: inoculating the endophytic fungus FO-R20 under the deposit number CCTCC M 2021505 into a liquid fermentation medium and culturing to obtain a fermentation broth, and then inoculating the fermentation broth on sterile barley grains and cultivating in the dark until mycelia grow and the grains are covered with mycelia to obtain the FO-R20 solid fungal fertilizer; and the liquid fermentation medium contains 0.4% of soybean cake flour, 1% of corn flour, 0.05% of magnesium sulfate and 0.1% of dipotassium phosphate per 250 mL of the medium by mass percentage.

Preferably, the fermentation broth and the sterile barley grains are mixed in a ratio of 100 mL:500 g and cultured at 25° C. in the dark until mycelia grow and the grains are covered with mycelia to obtain the FO-R20 solid fungal fertilizer.

It was found in the study of the present invention that after the colonization of the endophytic fungus FO-R20 in the root tissues of rice, the quality of rice seedlings was significantly improved, i.e., traits like the caudex width, chlorophyll content and seedling age of the seedlings were significantly improved.

Therefore, a method of the endophytic fungus FO-R20 is provided herein in enhancing quality of rice seedlings.

Further, the method comprises: preparing a seed coating agent with the endophytic fungus FO-R20, then mixing the seed coating agent with rice seeds and placing the seeds at a cool and ventilated place for air drying to obtain coated seeds, and then obtaining rice seedlings by seedling raising from the coated seeds;

alternatively, preparing a solid fungal fertilizer with the endophytic fungus FO-R20, and then mixing the solid fungal fertilizer with a seedling substrate to obtain a mixed substrate, in which germinated rice seeds are sown for seedling raising and cultivation to obtain rice seedlings.

Preferably, when preparing the coated seeds, the sterilized seeds are mixed well with the seed coating agent in a ratio of 2.5 g:1 mL, and after coating, the seeds are placed at a cool and ventilated place for air drying at 15-28° C.; and when preparing the mixed substrate, the solid fungal fertilizer and the seedling substrate are mixed in a mass ratio of 1:9.

It is further demonstrated by the study of the present invention that after colonization of the endophytic fungus FO-R20 in the root tissues of rice, a yield-increasing effect was seen, with the actual yield increased by up to 6.29%.

Therefore, a method of the endophytic fungus FO-R20 is provided herein in enhancing rice yields.

Further, the method comprises: preparing a seed coating agent with the endophytic fungus FO-R20, then mixing the seed coating agent with rice seeds and placing the seeds at a cool and ventilated place for air drying to obtain coated seeds, and then sowing the coated seeds directly in a field via direct seeding, and cultivating the seeds till harvest;

alternatively, preparing a solid fungal fertilizer with the endophytic fungus FO-R20, then mixing the solid fungal fertilizer with a seedling substrate, and sowing germinated rice seeds in the seedling substrate for seedling raising, and then transplanting rice seedlings into a field for cultivation till harvest.

The beneficial effects of the present invention are as follows.

The present invention provides a novel endophytic fungal strain FO-R20 in the genus *Phialophora*. Colonization of the endophytic fungus FO-R20 in the root tissues of rice can significantly improve the quality of rice seedlings and enhance rice yields. The remarkable effect of symbiosis and interactions of the endophytic fungus FO-R20 on rice has huge value in the agricultural field by application and popularization thereof.

DESCRIPTION OF THE EMBODIMENTS

The present invention is further described hereinafter in combination with detailed examples, but the present invention is not limited hereto. Unless otherwise specified, the technical means adopted in the examples are all regular technical means in the field, and the reagents are all commercially available.

Example 1 Isolation and Identification of Endophytic Fungal Strain FO-R20

I. Isolation and Purification of Endophytic Fungus FO-R20

The endophytic fungus FO-R20 was isolated from the root system of wild rice *Oryza granulata* (collected from Xishuangbanna, Yunnan Province, China).

The detailed method of isolation was as follows. Firstly, the root system of the wide rice was continuously rinsed with tap water and the soil particles and appendages were removed carefully. Healthy root tissues were picked for surface sterilization, and were immersed in 75% ethanol for 1-2 min and 1% sodium hypochlorite for 4-5 min, and subsequently rinsed with sterile deionized water three times. The root tissues were cut into 0.5 cm long segments, which were then transferred into 2% malt extract agar (MEA, OXOID; with 50 mg/L of chloramphenicol added to the medium to inhibit the growth of endophytic bacteria) plates for incubation at 25° C. in the dark. Endopytic fungal mycelia emerged from the edge of the tissue cuts on the fifth day of incubation, and were carefully picked with an inoculation loop and transferred into a fresh PDA medium for purification and cultivation. The strain was recorded as FO-R20.

The PDA medium contained 20 g/L of dextrose, 200 g/L of potatoes and 15 g/L of agar. The potatoes (200 g/L) were weighed according to the volume of the medium to be prepared, and were boiled, mashed, dissolved and filtered, then added with dextrose and agar, and autoclaved at 121° C. for 20 min.

II. Identification of Strain

1. Morphological Identification

Figure 1:
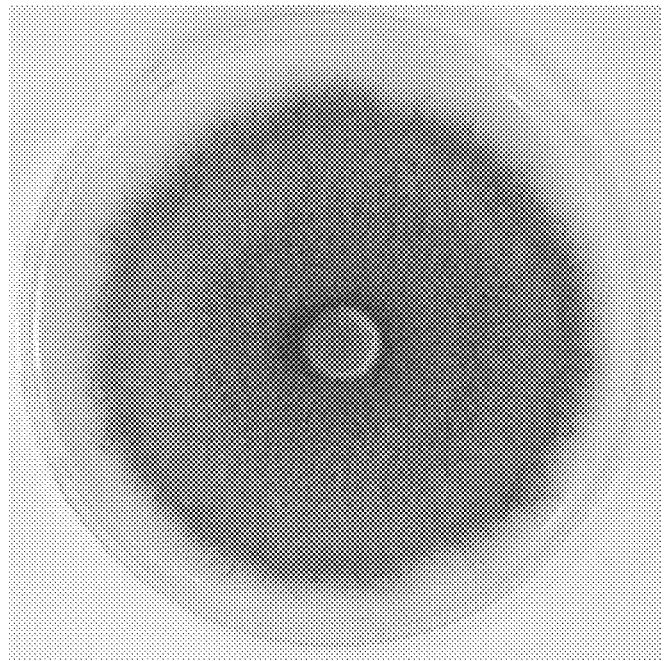
FIG. 1 shows an image of the colony morphology of the endophytic fungus FO-R20.
Figure 2:
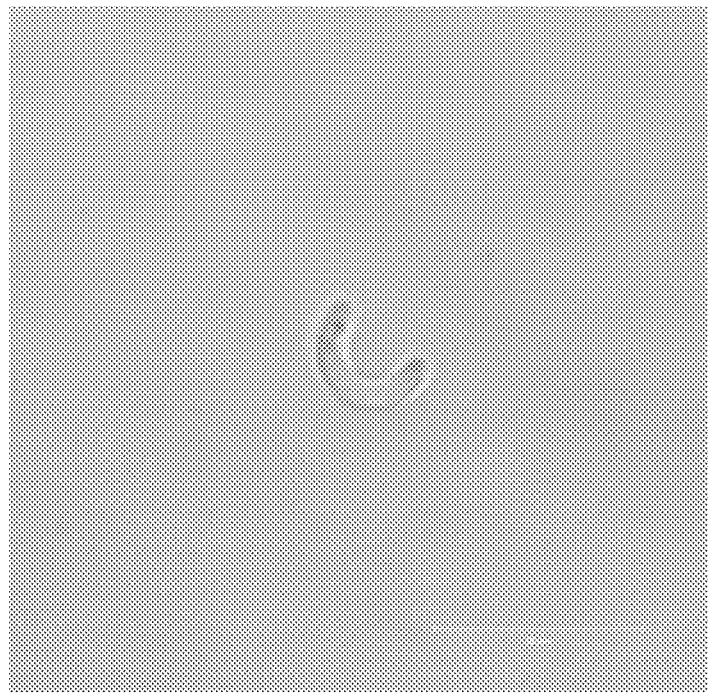
FIG. 2 shows an optical microscope image of conidia morphology of the endophytic fungal strain FO-R20, where the bar is 10 μm.
Figure 3:
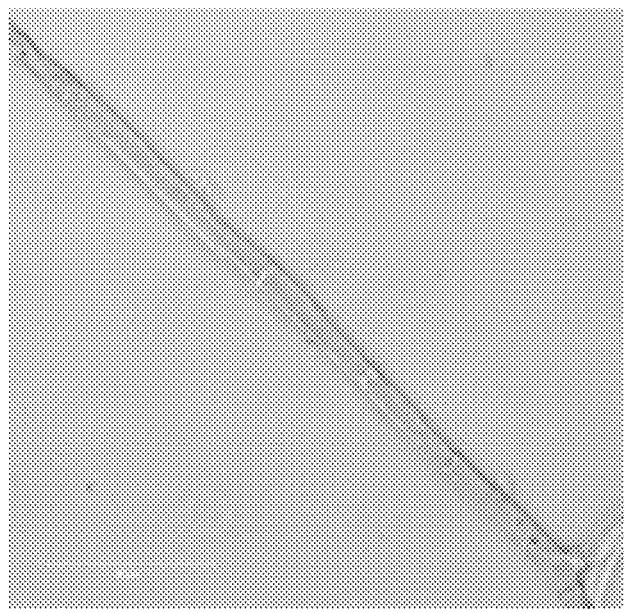
FIG. 3 shows an optical microscope image of mycelia morphology of the endophytic fungal strain FO-R20, where the bar is 20 μm.
Figure 4:
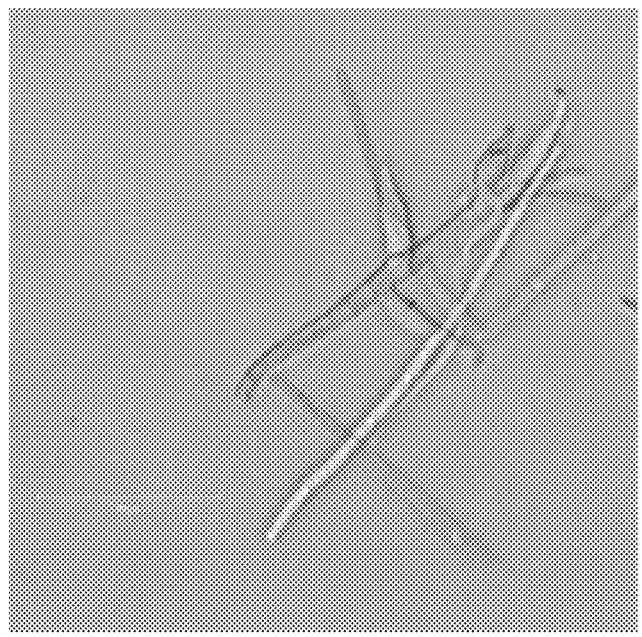
FIG. 4 shows an optical microscope image of morphology of the bottle-shaped sporophores of the endophytic fungal strain FO-R20, where the bar is 20 μm.

The isolated and purified strain FO-R20 was inoculated on a PDA medium and cultivated at 25° C. for 7 days. A small amount of the fungal mass was picked with an inoculation loop to prepare a slide for observation, measurement and imaging under an optical microscope. The growth status of the colony is shown in FIG. 1, and the morphology of conidia, mycelia and sporophores are shown in FIGS. 2, 3 and 4, respectively.

The morphological characteristics thereof are that, the colony of strain FO-R20 grew slowly on the PDA plate and the colony diameter reached 6 cm after growing on the PDA plate at 25° C. for 10 days; aerial mycelia were poorly developed, prostrating on the medium surface, and the colony was brown, the mycelia were hyaline or dark brown, 1.0-2.5 μm in width; conidiophores were bottle-shaped, solitary, unbranched, 5.0-13.5×2.5-3.0 μm; conidia were sickle-shaped, colorless, no septum, 7.0-9.0×0.8-1.2 μm.

2. Molecular Identification (1) DNA Extraction

① After the culture of strain FO-R20 on the PDA plate at 25° C. for 7 days, the mycelia were collected from the plate with a tooth pick and transferred into a sterilized 1.5 mL centrifuge tube containing 300 μL extraction buffer (1 M KCl, 100 mM Tris-HCl, 10 mM EDTA, pH=8.0).

② The fungal mass was pulverized with an electric grinder and vigorously vortexed for 2 min.

③ The pulverized mass was centrifuged at 10000 rpm for 10 min.

④ The supernatant was pipetted to a second clean centrifuge tube, and the precipitate was discarded.

⑤ Isopropanol (AR) was added to the supernatant in an equal volume, and mixed by inverting the tube gently several times, then centrifuged at 12000 rpm for 10 min to precipitate the nucleic acid.

⑥ The supernatant was discarded gently, and the centrifuge tube containing the precipitate was put on an absorbent paper upside down to drain water.

⑦ Subsequently, 300 μL 70% ethanol was added and mixed with the precipitate by inverting the tube gently several times and then centrifuged at 12000 rpm for 2 min.

⑧ The supernatant was discarded gently, and step ⑦ was repeated once.

⑨ The centrifuge tube was placed on an absorbent paper upside down to drain water, and placed at 37° C. for 15 min such that ethanol was fully evaporated.

⑩ The precipitate was resuspended in 50 μL ddH$_2$O to obtain the genomic DNA of FO-R20 with a concentration up to 30 ng/μL.

(2) PCR Amplification of Fungal ITS rDNA Gene

The PCR amplification was performed in a 50 μL reaction system containing: 2 μM each of an upstream primer and a downstream primer, 200 μM of dNTPs, 1.5 mM of MgCl$_2$, 5 μL of 10×PCR buffer, 2 μL of template DNA, and 2 U of Taq enzyme.

```
                                        (SEQ ID No. 2)
The sequence of the upstream primer ITSI was
5'- TCCGTAGGTGAACCTGCGG -3', and
                                        (SEQ ID No. 3)
the sequence of the downstream primer ITS4 was
5'- TCCTCCGCTTATTGATATGC -3'.
```

The PCR amplification reaction was carried out with a Longgene MG96G PCR cycler. The PCR cycling conditions consisted of: pre-denaturation at 94° C. for 2 min; then 35 cycles of denaturation at 94° C. for 30 seconds, annealing at 55° C. for 40 seconds and extension at 72° C. for 1 min; and a final extension at 72° C. for 10 min.

(3) Recovery and Purification of PCR Products

After the completion of the PCR reactions, the PCR products were checked by electrophoresis in 1% agarose gel, and then recovered and purified with the DNA gel purification kit of Axygen Biotechnology Limited, following the step-by-step procedure provided in the kit instructions.

(4) Gene Sequencing and Sequence Analysis

The purified and recovered target DNA fragments checked by electrophoresis were delivered to Sangon Biotech (Shanghai) for sequencing with an ABIPRISMA377 automatic sequencer. After strict check of the sequencing result, a DNA fragment sequence as shown in SEQ ID No.1 with a length of 527 bp was obtained.

Homologous or similar nucleotide sequences were searched for and aligned to the obtained nucleotide sequence by BLAST in the GenBank database on the national center for biotechnology information (NCBI) website. According to the BLAST alignment, the strain was identified as belonging to the genus *Phialophora*, with a percentage coverage of 100% and an identity up to 100% between the obtained sequence and the sequence under accession number NR_153972.1.

As demonstrated by the results of the above molecular identification and morphological identification, the newly isolated strain belongs to the genus *Phialophora* in the family Magnaporthaceae in the class Sordariomycetes in the phylum Ascomycota in the kingdom Fungi. The strain was designated with the scientific name *Falciphora oryzae* FO-R20, and was deposited on May 8, 2021 in the China Center for Type Culture Collection (CCTCC) at Wuhan University in Wuhan, China, the recognized IDA under the Budapest Treaty on the International Recognition of the Deposit of Microorganisms for the Purposes of Patent Procedure, under the deposit number of CCTCC M 2021505.

Example 2 Seedling Raising by Using Strain FO-R20 Coating Agent

Test Plant: A Regular Rice Cultivar, Chunyou 927, of *Oryza sativa* L.

1. Culture of Strain FO-R20 and Liquid Fermentation

Strain FO-R20 preserved on a filter paper sheet was inoculated on a potato dextrose agar (PDA) solid medium to be activated through culturing at 25° C. for 7 days in the dark. Plugs were punched with a 0.5 cm diameter hole punch, and (5 plugs) were inoculated into an Erlenmeyer flask containing 500 mL of a liquid fermentation medium, and incubated in a shaker (set at 25° C. and at a speed of 150) for 7 days. Next, the liquid fermentation broth was vacuum filtered to remove the medium and obtain the mycelia. 0.1 g mycelia were weighed, and the moisture content was measured as 80% for calculation of the dry weight of mycelia.

The PDA medium contained 20 g/L of dextrose, 200 g/L of potatoes and 15 g/L of agar. The potatoes (200 g/L) were weighed according to the volume of the medium to be prepared, and were boiled, mashed, dissolved and filtered, then added with dextrose and agar, and autoclaved at 121° C. for 20 min.

The liquid fermentation medium was prepared with 0.4% of soybean cake flour, 1% of corn flour, 0.05% of magnesium sulfate and 0.1% of dipotassium phosphate in proportion, and supplemented with water to give 250 mL of the medium; the medium was subjected to moist heat sterilization at 120° C. for 15 min.

2. Preparation of FO-R20 seed coating agent: the seed coating agent was obtained by mixing the mycelia with a 1% chitosan solution in a ratio of 1:10000 (dry weight:volume), that is, mixing 1 g of mycelia by dry weight and 10 L of 1% chitosan solution to obtain the seed coating agent. Since the moisture content of mycelia after vacuum filtration varies, the seed coating agent was prepared each time according to the calculated dry weight of mycelia.

The formulation of the 1% chitosan solution was as follows: dissolving 1 g of chitosan in 100 mL of 1% acetic acid solution.

Figure 5:
FIG. 5 shows the endophytic fungus FO-R20 seed coating agent in Example 2. Left: sterilized rice seeds; right: FO-R20 seed coating agent.
Figure 6:
FIG. 6 shows the seeds coated by the endophytic fungus FO-R20 in Example 2.

3. Seed coating treatment: the surface of rice seeds was disinfected with 1% sodium hypochlorite for 10 min, rinsed well with water and drained, as shown in FIG. 5, and then the disinfected seeds were mixed with the seed coating agent in a ratio of 2.5:1 (weight:volume), i.e., use 1 mL of the seed coating agent for every 2.5 g of seeds to obtain coated seeds. As shown in FIG. 6, the coated seeds were spread on sterile gauze and placed in a cool and ventilated place (15-28° C.) for air drying for 2-3 days.

4. The coated seeds were uniformly sown in a seedling tray by the means of seedling raising in a substrate, and cultivated for 25-28 days with normal water and fertilizer management, and no fungicide was applied during the entire period of seedling raising.

5. Determination of quality of seedlings

Figure 7:
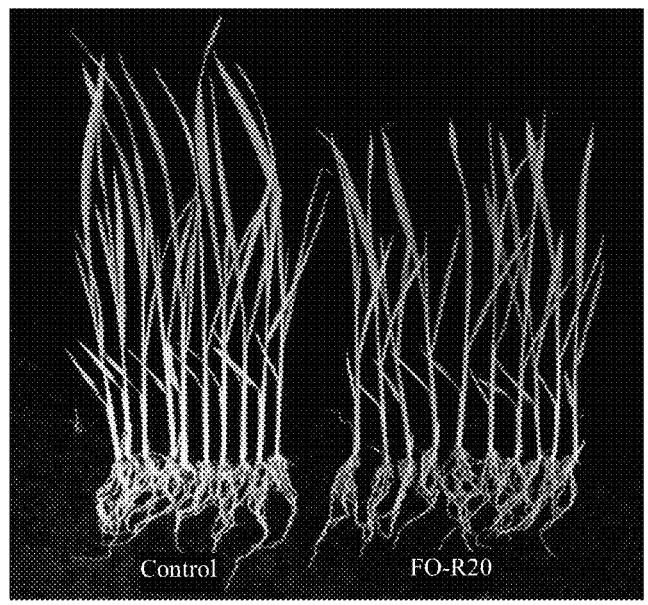
FIG. 7 shows pictures demonstrating the influence of the endophytic fungus FO-R20 coating agent on rice seedlings in Example 2.
Figure 8:
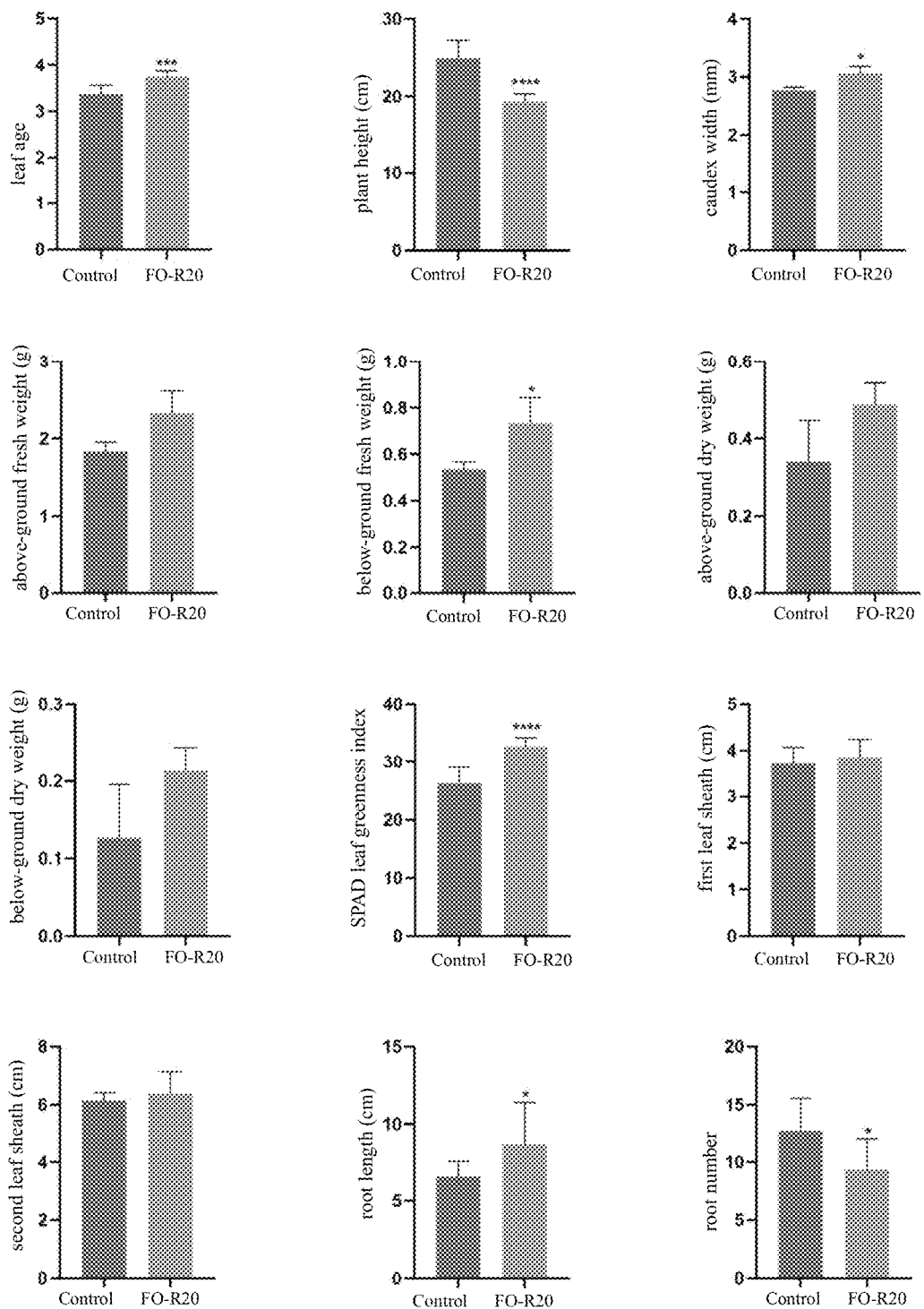
FIG. 8 shows the influence of the endophytic fungus FO-R20 coating agent on the quality of rice seedlings in Example 2, wherein the quality of rice seedlings includes: leaf age, plant height, caudex width, above-ground fresh weight, below-ground fresh weight, above-ground dry weight, below-ground dry weight, the SPAD leaf greenness index, length of first leaf sheath, length of second leaf sheath, root length, and root number. The significance was determined by a t-test, wherein * denotes $P<0.05$,  denotes $P<0.01$, * denotes $P<0.001$, and ** denotes $P<0.0001$.

The demonstration field of seedling raising by using the endophytic fungal coating agent was located in the Pingyao area of Hangzhou City in Zhejiang Province in China, with uncoated rice seeds as the control. The sowing date was May 23, and the seedling raising lasted for 25 days. It was found that the rice seedlings treated with the endophytic fungal coating were robust and balanced, with no obvious incidence of pest or disease, as shown in FIGS. 7 and 8.

Example 3 Seedling Raising with FO-R20 Solid Fungal Fertilizer

Test Plant: Nangeng 5055 of Rice *Oryza sativa* L.

1. Culture and Fermentation of Strain FO-R20

Strain FO-R20 preserved on a filter paper sheet was inoculated on a potato dextrose agar (PDA) solid medium to be activated through culturing at 25° C. for 7 days in the dark. Plugs were punched with a 0.5 cm diameter hole punch, and (5 plugs) were inoculated into an Erlenmeyer flask containing 500 mL of a liquid fermentation medium, and incubated in a shaker (set at 25° C. and at a speed of 150) for 7 days. Then the liquid fermentation broth was inoculated in a culture bottle containing sterile wheat grains (500 g of wheat grains/bottle, 100 mL of fermentation broth: 500 g of wheat grains), and incubated in a dark incubator at 25° C. for 10-15 days, until the mycelia grew such that the wheat grains were covered with the mycelia, and then set aside.

The PDA medium contained 20 g/L of dextrose, 200 g/L of potatoes and 15 g/L of agar. The potatoes (200 g/L) were weighed according to the volume of the medium to be prepared, and were boiled, mashed, dissolved and filtered, then added with dextrose and agar, and autoclaved at 121° C. for 20 min.

The liquid fermentation medium was prepared with 0.4% of soybean cake flour, 1% of corn flour, 0.05% of magnesium sulfate and 0.1% of dipotassium phosphate in proportion, and supplemented with water to give 250 mL of the medium; the medium was subjected to moist heat sterilization at 120° C. for 15 min.

2. Seedling Raising in Substrate with FO-R20 Solid Fungal Fertilizer

Figure 9:
FIG. 9 shows the endophytic fungus FO-R20 solid fungal fertilizer in Example 3.

The fermented solid fungal fertilizer (FIG. 9) was mixed with a regular seedling substrate and spread in a seedling tray, each seedling tray containing 10 g of solid fungal fertilizer. The rice seeds were soaked in 3000-time diluted 25% phenamacril for 2 days for seed disinfection, and then placed in a dark constant-temperature incubator set at 30° C. for 1-2 days to facilitate germination. When radicles emerged from the seeds, the seeds were uniformly sown in seedling trays and placed in a seedling field for seedling raising and cultivation, where the seeds were subjected to normal water management.

3. Determination of Quality of Rice Seedlings

Figure 10:
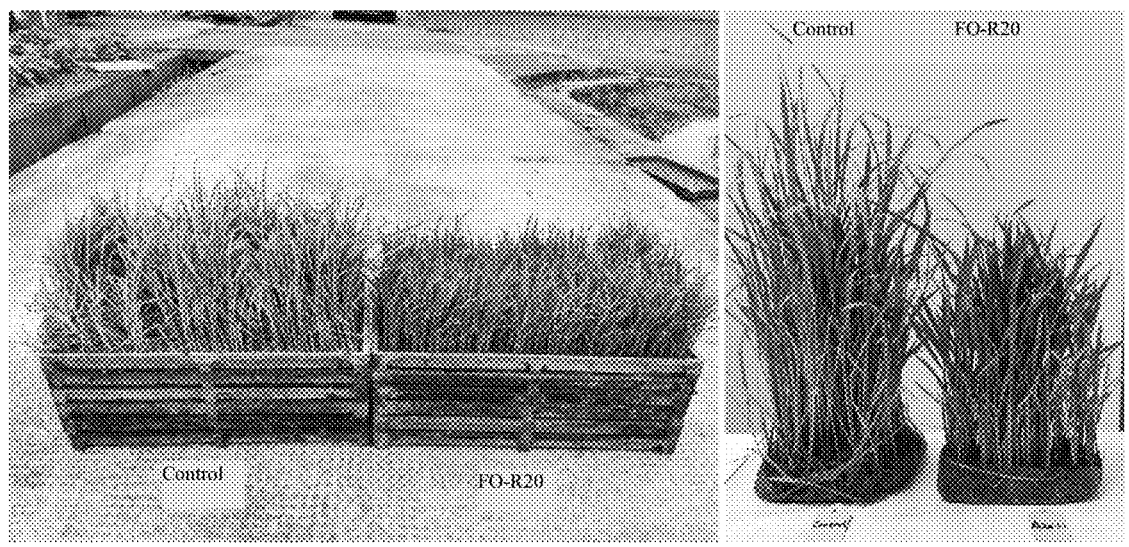
FIG. 10 shows the pictures demonstrating the influence of the endophytic fungus FO-R20 solid fungal fertilizer on rice seedlings in Example 3.
Figure 11:
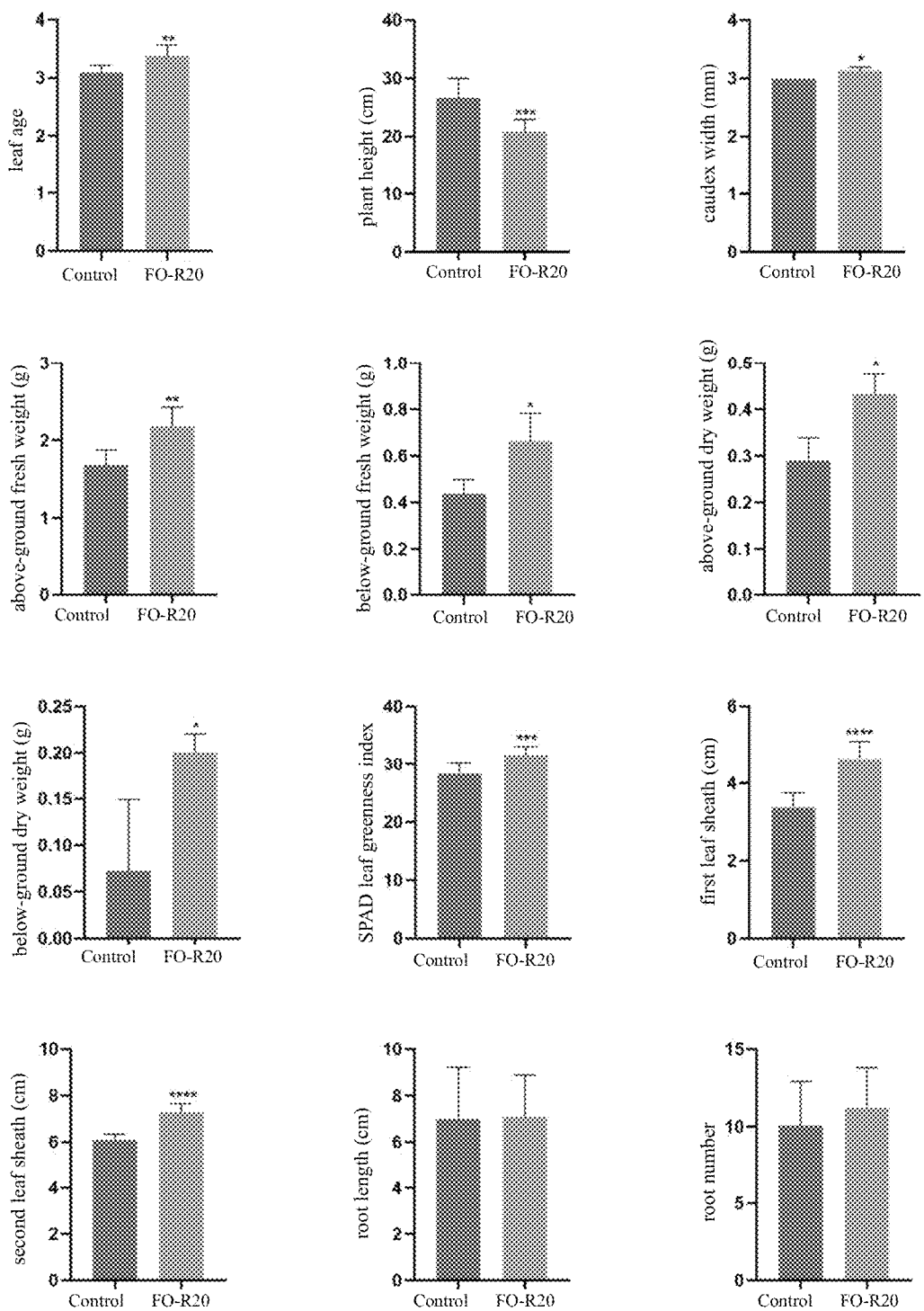
FIG. 11 shows the influence of the endophytic fungus FO-R20 solid fungal fertilizer on the quality of rice seedlings in Example 3. The significance was determined by a t-test, wherein * denotes $P<0.05$,  denotes $P<0.01$, * denotes $P<0.001$, and ** denotes $P<0.0001$.

After growth in the seedling trays for 23-25 days, the quality of the seedlings was determined. As shown in FIGS. 10 and 11, the rice seedlings treated with the solid fungal fertilizer prepared with the endophytic fungus were found to be robust and balanced, with no obvious incidence of pest or disease.

Example 4 Influence of Strain FO-R20 Coating Agent on Rice Yields

Test Plant: A Hybrid Cultivar, Yongyou 538, of *Oryza sativa* L.

1. Culture and fermentation of strain FO-R20, preparation of the seed coating agent, and seed coating treatment were the same as in Example 2.
2. The coated seeds were uniformly sown in a field by the means of direct and manual seeding, cultivated till harvest with normal water and fertilizer management, and no fungicide was applied during the entire growth duration. The seed dosage was 2 kg per Mu (Mu is a unit of area that is commonly used in China. 1 Mu is about 666.7 m$^2$).

Figure 12:
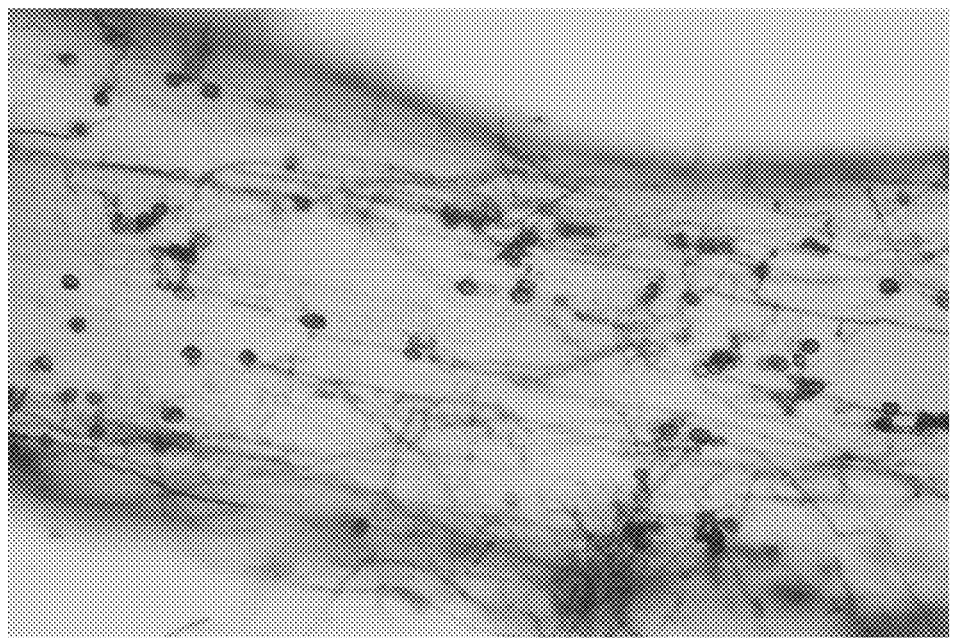
FIG. 12 shows colonization of the endophytic fungus FO-R20 in rice roots.

Additionally, to ensure that the fungus could colonize the roots, seedlings were pulled out 15 days after sowing, the root system was cleaned and a small portion of the roots were cut to obtain a sample to be observed under an LSM780 fluorescence confocal microscope (Carl Zeiss Inc., Jena, Germany) for microscopic examination of colonization of the fungus FO-R20 in the roots (FIG. 12).

3. Determination of rice yields

Figure 13:
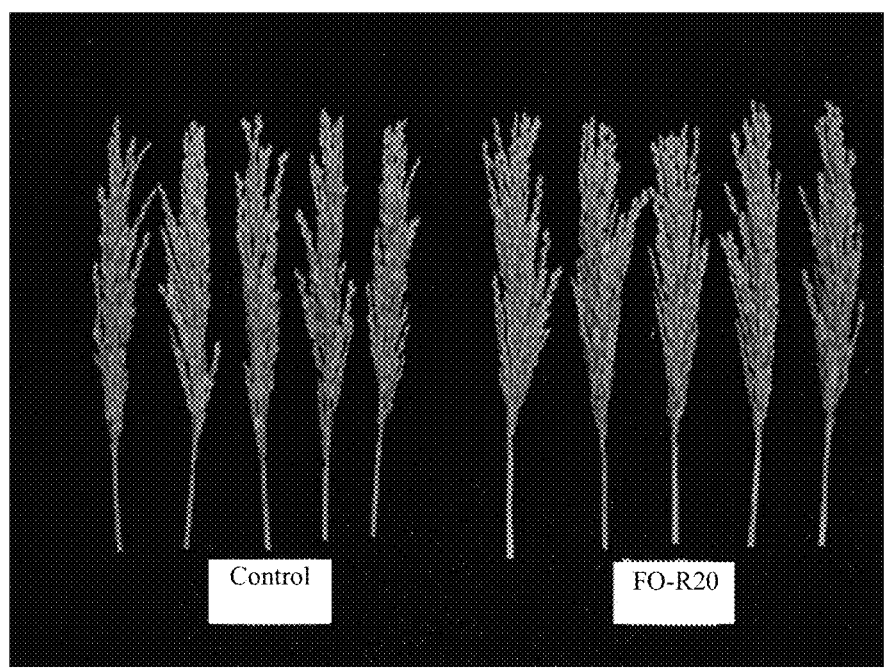
FIG. 13 shows the influence of the endophytic fungus FO-R20 coating agent on rice grains in Example 4.

The demonstration field of seedling raising by using the endophytic fungal coating agent was located in Jiangnan Town, Tonglu County, Hangzhou City, Zhejiang Province, China, the total area being 60 Mu, with uncoated seeds as the control. The sowing date was June 23, and the maturity date was November 6. It was found that at the time of ripe, the rice treated with coating by the endophytic fungus was robust and balanced, with green stems and yellow ripe and no obvious incidence of pest or disease, having enhanced panicle length and plump grains (FIG. 13).

Theoretical yield determination: the average theoretical unit yield of rice treated with endophytic fungal coating was 614.37 kg/Mu, and the average theoretical unit yield of the control group which was not treated with endophytic fungal coating was 580.84 kg/Mu, hence giving a theoretical yield increase of 5.77% (Table 1).

Actual yield determination: one rice field treated with the endophytic fungal seed coating agent was used, as well as one control field, the area of the fields being 1.0015 Mu and 1.0064 Mu, respectively. After mechanical harvesting of the whole field, the actual water content of rice was measured and the rice was weighed. Calculated based on a deduction of impurities by 1.0% and a water content of 13.5% in the Indica-Japonica hybrid rice, the actual yield of the rice produced by direct seeding and treated with the endophytic fungal coating agent was 564 kg/Mu, and the actual yield of the control was 542 kg/mu, hence giving an actual yield increase of 4.06%.

Hundred-Mu yield determination: according to the rice yield determination and acceptance method of the Ministry of Agriculture and Rural Affairs of China, the yield of single-season rice produced by direct seeding and treated with endophytic fungal coating was determined in an area of 100 Mu, and according to the results in Table 2, the arithmetic average yield of rice in the demonstration field was 662.4 kg/Mu.

TABLE 2

Results of yield determination of rice treated with endophytic fungus FO-R20 coating agent in hundred-Mu demonstration field

| | Area (Mu) | Wet grain weight (kg) | Water | Impurity (%) | Converted dry grain yield (kg) |
|---|---|---|---|---|---|
| Field 1 | 1.0032 | 798 | 27.62 | 1% | 658.9 |
| Field 2 | 1.2614 | 1020 | 28.12 | 1% | 665.19 |
| Field 3 | 1.042 | 830 | 27.26 | 1% | 663.10 |

Example 5 Influence of FO-R20 Solid Fungal Fertilizer on Rice Yields

Test plant: a hybrid cultivar, Yongyou 1450, of *Oryza sativa* L.

1. Culture and fermentation of strain FO-R20, and seedling raising in a substrate were the same as in Example 3.
2. Transplanting rice seedlings After growth in the seedling trays for 23-25 days, the seedlings were pulled out and transplanted into fields. The seedlings were transplanted in such a manner that there were 3 seedlings per cluster, with a distance of 10-15 cm between clusters and 30 cm between rows. The seedlings were cultivated till harvest with normal water and fertilizer management, and no fungicide was applied during the entire growth duration.

3. Determination of rice yields

Figure 14:
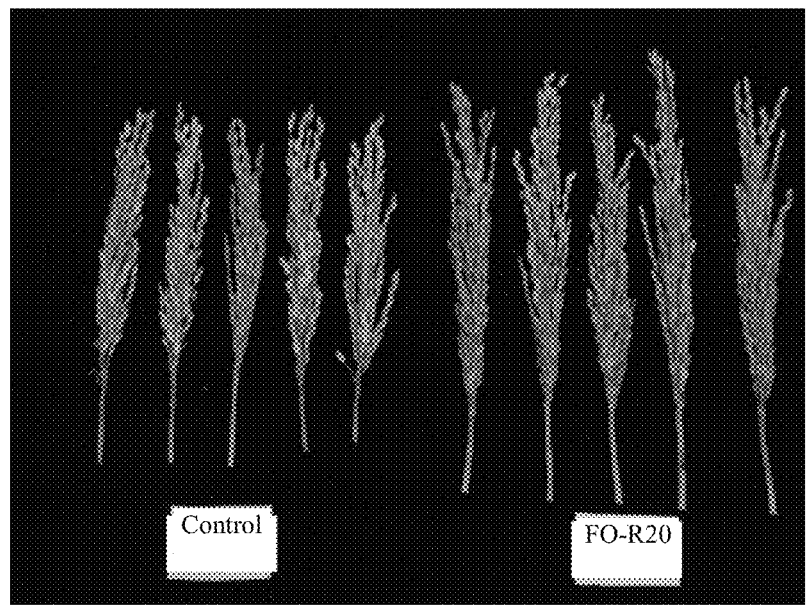
FIG. 14 shows the influence of the endophytic fungus FO-R20 solid fungal fertilizer on rice grains in Example 5.

The demonstration field of seedling raising by using the endophytic fungal fertilizer was located in Wangshantou Village, Quanxi Town, Wuyi County, Jinhua City, Zhejiang Province, China, the total area being 160 Mu, with mechanical planting of seedlings raised in regular nutritious soil as the control. The sowing date was June 23, the mechanical planting date was July 18, and the ripe date was November 14. It was found that at the time of ripe, the late rice of succession cropping by mechanical planting of seedlings raised by using the endophytic fungus was robust and balanced, with green stems and yellow ripe and no obvious incidence of pest or disease, having enhanced panicle length and plump grains (FIG. 14).

Theoretical yield determination: the average theoretical unit yield of rice treated with the solid fungal fertilizer prepared with the endophytic fungus for seedling raising was 687.01 kg/Mu, and the average theoretical unit yield of the control group which was not treated with the endophytic fungal fertilizer was 651.07 kg/Mu, with a theoretical yield increase of 5.52% (Table 3).

TABLE 1

Theoretical yield increase of rice by the endophytic fungus FO-R20 coating agent

| Name | Number of clusters per Mu | Panicle length (cm) | Number of panicles per cluster | Total grain number per panicle | Number of filled grains per panicle | Seed setting rate (%) | Thousand grain weight (g) | Average theoretical yield (kg/Mu) |
|---|---|---|---|---|---|---|---|---|
| FO-R20 | 11116.67 | 20.5 | 10.00 | 380.56 | 282.78 | 74.38 | 21.95 | 614.37 |
| Control | 11116.67 | 20.5 | 9.00 | 337.63 | 243.50 | 72.12 | 21.69 | 580.84 |

TABLE 3

Theoretical yield increase of rice by the solid fungal fertilizer prepared with the endophytic fungus FO-R20

| Name | Number of clusters per Mu | Panicle length (cm) | Number of panicles per cluster | Total grain number per panicle | Number of filled grains per cluster | Seed setting rate (%) | Thousand grain weight (g) | Average theoretical yield (kg/Mu) |
|---|---|---|---|---|---|---|---|---|
| FO-R20 | 11116.67 | 21.33 | 11.00 | 270.76 | 222.94 | 74.38 | 25.20 | 687.01 |
| Control | 11116.67 | 19.44 | 13.00 | 223.94 | 183.63 | 82.00 | 24.53 | 651.07 |

Actual yield determination: one rice field treated with the solid fungal fertilizer prepared with the endophytic fungus for seedling raising was used, as well as one control field, the area being 1.0657 Mu and 1.0275 Mu, respectively. After mechanical harvesting of the whole field, the actual water content of rice was measured and the rice was weighed. Calculated based on a deduction of impurities by 1.0% and a water content of 13.5% in the Indica-*Japonica* hybrid rice, the actual yield of the rice, which was produced via mechanical planting and seedling raising by the solid fungal fertilizer prepared with the endophytic fungus, was 597.9 kg/Mu, and the actual yield of the control was 562.5 kg/Mu, hence giving an actual yield increase of 6.29%.

Hundred-Mu yield determination: according to the rice yield determination and acceptance method of the Ministry of Agriculture and Rural Affairs of China, the yield of the late rice of succession cropping by mechanical planting of seedlings raised by using the endophytic fungus substrate was determined in an area of 100 Mu, and according to the results in Table 4, the arithmetic average yield of rice in the demonstration field was 658.6 kg/Mu.

TABLE 4

Results of yield determination of rice treated with solid fungal fertilizer prepared with endophytic fungus FO-R20 in hundred-Mu demonstration field

| | Area (Mu) | Wet grain weight (kg) | Water | Impurity (%) | Converted dry grain yield (kg) |
|---|---|---|---|---|---|
| Field 1 | 0.9636 | 770 | 27.52 | 1% | 669.8 |
| Field 2 | 1.4674 | 1155 | 28.02 | 1% | 648.4 |
| Field 3 | 1.342 | 1060 | 27.26 | 1% | 657.6 |

The above examples are merely preferred examples of the present invention, but not all examples. All other embodiments obtained by those skilled in the art based on the examples in the embodiments without inventive effort are within the protection scope of the present invention.

The invention claimed is:

1. A method to enhance quality of rice seedlings comprising: preparing a seed coating agent with the endophytic fungus FO-R20, then mixing the seed coating agent with rice seeds and placing the seeds at a ventilated place for air drying to obtain coated seeds, followed by raising seedling from the coated seeds to obtain rice seedlings;
   wherein the deposit number for the endophytic fungus FO-R20 is CCTCC M 2021505 and the scientific name thereof is *Falciphora oryzae;*
   wherein the endophytic fungus FO-R20 seed coating agent is made by a preparation method comprising: obtaining a seed coating agent after mixing mycelia of an endophytic fungus FO-R20 under the deposit number CCTCC M 2021505 with a chitosan solution;
   wherein the endophytic fungal strain FO-R20 is inoculated in a potato dextrose agar medium and cultured at 25° C. in the dark, and then inoculated in a liquid fermentation medium and cultured at 25° C. to obtain mycelia of the endophytic fungus FO-R20; then the mycelia are mixed with the chitosan solution at a mass percentage concentration of 1% in a ratio of 1 g:10 L to obtain the seed coating agent, where 1% refers to the amount of chitosan in the chitosan solution and the ration 1 g:10 L refers to the ration of grams mycelia to liters of 1% chitosan solution; and
   the liquid fermentation medium contains 0.4% soybean cake flour, 1% corn flour, 0.05% magnesium sulfate and 0.1% dipotassium phosphate per 100 mL of the medium by mass concentration (w/v).

2. A method to enhance quality of rice seedlings comprising: preparing a solid fungal fertilizer with the endophytic fungus FO-R20, and then mixing the solid fungal fertilizer with a seedling substrate to obtain a mixed substrate, in which germinated rice seeds are sown for cultivation to obtain rice seedlings;
   wherein the deposit number for the endophytic fungus FO-R20 is CCTCC M 2021505 and the scientific name thereof is *Falciphora oryzae;*
   wherein the endophytic fungus FO-R20 solid fungal fertilizer is made by a preparation method comprising: inoculating an endophytic fungus FO-R20 under the deposit number CCTCC M 2021505 into a liquid fermentation medium and culturing to obtain a fermentation broth, then inoculating the fermentation broth on sterile barley grains and culturing in the dark until mycelia grow and the grains are covered with mycelia to obtain the FO-R20 solid fungal fertilizer; and
   the liquid fermentation medium contains 0.4% of soybean cake flour, 1% of corn flour, 0.05% of magnesium sulfate and 0.1% of dipotassium phosphate per 100 mL of the medium by mass concentration (w/v).

3. The method according to claim 1, wherein volume of the liquid fermentation is 250 ml.

4. The method according to claim 2, wherein volume of the liquid fermentation is 250 ml.

* * * * *